(12) United States Patent
Butaric et al.

(10) Patent No.: US 7,399,314 B2
(45) Date of Patent: Jul. 15, 2008

(54) SYSTEMS AND METHODS FOR SECURING GRAFT MATERIAL TO INTRALUMINAL DEVICES

(75) Inventors: Frank Butaric, Pembroke Pines, FL (US); I. John Khan, Bridgewater, NJ (US); Diana M. Sanchez, Bernardsville, NJ (US)

(73) Assignee: Cordis Corporation, Miami Lakes, FL (US)

( * ) Notice: Subject to any disclaimer, the term of this patent is extended or adjusted under 35 U.S.C. 154(b) by 417 days.

(21) Appl. No.: 11/274,076

(22) Filed: Nov. 15, 2005

(65) Prior Publication Data

US 2007/0112410 A1    May 17, 2007

(51) Int. Cl.
*A61F 2/06* (2006.01)
(52) U.S. Cl. .................................................. 623/1.13
(58) Field of Classification Search ............... 623/1.13, 623/1.49–1.51
See application file for complete search history.

(56) References Cited

U.S. PATENT DOCUMENTS

| | | | | |
|---|---|---|---|---|
| 2004/0054396 A1* | 3/2004 | Hartley et al. | ............... | 623/1.13 |
| 2004/0106978 A1* | 6/2004 | Greenberg et al. | ......... | 623/1.13 |
| 2005/0159803 A1* | 7/2005 | Lad et al. | ................... | 623/1.13 |
| 2005/0159804 A1* | 7/2005 | Lad et al. | ................... | 623/1.13 |

* cited by examiner

*Primary Examiner*—Suzette J Gherbi
(74) *Attorney, Agent, or Firm*—Carl J. Evens

(57) ABSTRACT

A stent graft having graft material attached to a stent structure while providing a low profile to the stent graft in its crimped state. The graft material may be attached to an internal surface, an external surface, or both the internal surface and the external surface of the stent. The graft material may cover all or part of such surfaces. The stent graft is expandable upon delivery to the intended treatment site. The expandable nature of the stent graft may be accomplished by self-expanding materials, or through other methods, such as balloon expansion, as generally practiced in the art. The stent graft material is comprised of durable biocompatible materials as generally practiced in the art. The stent graft in its crimped state comprises a low profile fluid flow conduit that is preferably percutaneously delivered, but that may be surgically emplaced to the intended treatment site. Interdigitable stitches on alternating struts of a stent, heat riveted sutures in combination with a preformed hole in a portion of the stent and a washer, or a combination of the interdigitable stitches and the heat riveted sutures and corresponding preformed holes and washers are used to secure the graft material to the stent.

12 Claims, 4 Drawing Sheets

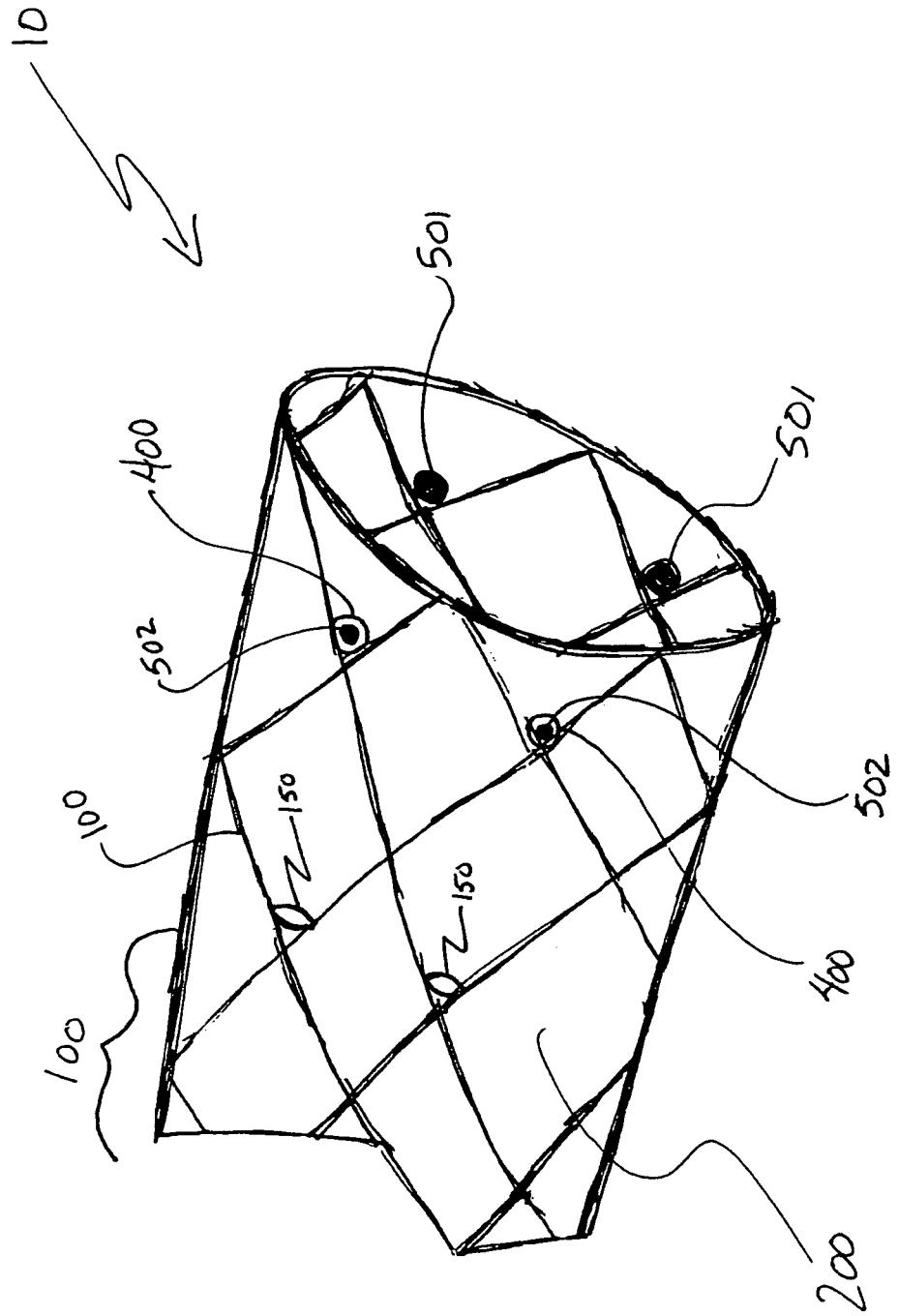

SYSTEMS AND METHODS FOR SECURING GRAFT MATERIAL TO INTRALUMINAL DEVICES

BACKGROUND OF THE INVENTION

1. Field of the Invention

The invention generally relates to systems and methods for securing graft material to intraluminal devices.

2. Related Art

Intraluminal devices are commonly used in the treatment of diseased or impaired blood vessels in order to improve the performance of the diseased or impaired blood vessel. Such vascular diseases or impairments may include stenosis, thrombosis, occlusion or an aneurysm. Stents are a typical intraluminal device used to treat such diseased or impaired blood vessels.

A stent is generally a tubular device formed of biocompatible material that is implanted into a vessel to open and support the vessel. A stent is typically open ended and radially expandable to a diameter larger than its insertion diameter. In some cases, a stent may include a graft, i.e., a material attached to the stent, in order to provide an artificial lumen through which blood flow proceeds. Such a graft is typically comprised of bio-compatible material, such as polytetrafluoroethylene (PTFE) or expanded PTFE (ePTFE), having a microporous structure that enable tissue ingrowth and endothelialization once implanted at the intended location in the vascular system. Often, the means of attaching the graft material to a stent reduces the flexibility of the intraluminal device and increases the width of the device.

In the case of an aneurysm, an abnormal dilation of a layer or layers of an arterial wall occurs, usually as a result of a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm, on the other hand, is an aneurysm in the thoracic portion of the aorta. When left untreated, the aneurysm may rupture, usually causing rapid fatal hemorrhaging.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft, via transperitoneal or retroperitoneal procedures, has been the standard treatment, it is associated with significant risk. For example, complications include myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and as high as fifty percent in patients with ruptured abdominal aortic aneurysms.

Disadvantages associated with conventional surgery, in addition to the high mortality rate, include an extended recovery period associated with the large incision and opening of the abdominal cavity, difficulties suturing the graft to the aorta, the loss of existing thrombosis to support and reinforce the graft, the unsuitability of certain patients for abdominal surgery, and the problems associated with such surgery after rupture of an aneurysm. The recovery and convalescent period often includes up to two weeks in the hospital and up to several months more at home, particularly if complications occur. Further, because many patients having abdominal aortic aneurysms are older, with other chronic illnesses, such patients are less than ideal candidates for such surgery.

Although abdominal aortic aneurysms are the most commonly occurring aneurysms, the occurrence of aneurysms is not limited to such abdominal regions. For example, thoracic aortic aneurysms also occur. Such thoracic aortic aneurysms require similar surgery, which is a major undertaking with associated high risks and significant mortality and morbidity.

Recently, less invasive, catheter-directed endovascular techniques have been developed for treating aneurysms, and abdominal aortic aneurysms in particular. The development of vascular stents, used in conjunction with graft material, has facilitated these less invasive treatment techniques. Shorter hospital stays, reduced periods of convalescence, and lower morbidity and mortality rates have occurred as a result.

The delivery procedure for such stent grafts typically involves advanced angiographic techniques performed through vascular accesses gained via surgical cutdown of a remote artery, such as the brachial or femoral artery. An appropriate sized introducer is placed over a guidewire and into the remote artery. Through the introducer, the stent graft is advanced to an intended treatment site via a delivery catheter. Typical deployment of the stent graft requires withdrawal of an outer sheath of the delivery catheter while maintaining the position of the stent graft with an inner stabilizing device. Most stent grafts are comprised of self-expanding materials; however, an additional angioplasty procedure, such as balloon angioplasty, may be required to secure the stent graft in place as desired at the intended treatment site. Thereafter, the introducer, guidewire, and the various components of the delivery catheter are withdrawn.

Due to the large diameters of the above described devices, typically greater than 20 French (3 F=1 mm), arteriotomy closure often requires open surgical repairs. Moreover, the manner in which the graft material is attached to the stent can undesirably increase the profile of the stent graft, rendering emplacement of the stent graft more difficult, and risking unintended and undesirable injury to the vessel during delivery and deployment to the intended treatment site.

In view of the above, a need exists for systems and methods that more reliably secure graft material to a stent structure without hindering the flexibility and radial stiffness of the stent graft. Ideally, such systems and methods would more reliably secure graft material to a stent structure in a manner enabling a reduction in the profile of the stent graft in a crimped state so as to improve the delivery and positioning of the stent graft at an intended treatment site.

SUMMARY OF THE INVENTION

The systems and methods of the invention comprise a stent graft having graft material attached to a stent structure while providing a low profile to the stent graft in its crimped state. The graft material may be attached to an internal surface, an external surface, or both the internal surface and the external surface of the stent. The graft material may cover all or part of such surfaces. The stent graft is expandable upon delivery to the intended treatment site. The expandable nature of the stent graft may be accomplished by self-expanding materials, or through other methods, such as balloon expansion, as generally practiced in the art. The stent graft material is comprised of durable biocompatible materials as generally practiced in the art. The stent graft in its crimped state comprises a low profile fluid flow conduit that is preferably percutaneously delivered, but that may be surgically emplaced to the intended treatment site.

In some embodiments, the stent graft comprises a graft material blanket stitched to alternating struts of the stent using an even:odd, or vice versa, ratio of stitches on the alternating struts. An even number of blanket stitches on a first strut are thus staggered relative to an odd number of blanket stitches on a neighboring strut so as to interdigitate the stitches on the alternating struts and provide a low profile of the stent graft when the stent graft is in its crimped state. The even:odd ratio, or vice versa, ratio of blanket stitches provided on the alternating struts is ideally 3:4 stitches for stent grafts having diameters less than 14 mm. The even:odd ratio, or vice versa, ratio of blanket stitches provided on the alternating struts is ideally 4:5 or 5:6 for larger diameter stent grafts having diameters between 14 mm to 30 mm. The even:odd ratio, or vice versa, ratio of blanket stitches provided on the alternating struts is ideally 6:7 or greater, depending on the application, for stent grafts having diameters greater than 30 mm. The blanket stitch length is based on the length of the stent strut that is being stitched along. The stitch ratio per alternating strut helps to accommodate crimping of the stent more fully. Of course, other ratios are contemplated and determined according to stent graft length or other medical and physiological needs.

In other embodiments, the graft material is attached to the stent with ends of one or more filament sutures heat riveted on an internal and an external side of the stent graft. The filament sutures thus penetrate through the graft material at designated voids of the stent, such as through a preformed hole in a portion of at least one strut of the stent and through the overlying graft material, whereby an internal end of each suture extends into a cavity formed by the internal sides of the stent graft and an opposite external end of each suture extends beyond the external side of the stent graft. The external end of a respective suture is placed through a washer that is placed over the graft material at a location through which the suture was threaded. The opposed internal and external ends of each suture are then heated to rivet the graft material to the stent, whereby the internal end of each filament is heat riveted before the respective external end thereof. Thereafter, the external ends of each filament suture is heat riveted. The heat riveted internal and external ends of the filament suture are larger in diameter than the opening of the washer and the preformed hole in the struts of the stent. The graft material is thus secured to the stent, between the respective preformed hole and washer through which the suture has been threaded, by the internal and external rivet sutures created by the heating of the ends of the suture. Because the internal and external rivet sutures are larger than the respective washer opening, the graft material is even more securely affixed to the stent. Inadvertent or undesirable micro-motions of the graft material relative to the stent structure is minimized as a result. The washers can comprise radiopaque materials to enhance visualization thereof during delivery and deployment of the stent graft. The stent graft having graft material secured in this manner may be a low profile stent with good flexibility and radial stiffness.

An alternative embodiment combines the even:odd stitch ratio technique with the heat rivet and washer technique for securing graft material to the underlying stent structure as otherwise referenced above. In any case, the stent graft can be crimped to a smaller insertion and delivery diameter, and expanded to a larger expanded deployed diameter at an intended treatment site while maintaining good flexibility and radial stiffness of the stent graft, and while minimizing undesirable micro-motions of the graft material relative to the underlying stent structure.

The above and other features of the invention, including various novel details of construction and combinations of parts, will now be more particularly described with reference to the accompanying drawings and claims. It will be understood that the various exemplary embodiments of the invention described herein are shown by way of illustration only and not as a limitation thereof. The principles and features of this invention may be employed in various alternative embodiments without departing from the scope of the invention.

BRIEF DESCRIPTION OF THE DRAWINGS

These and other features, aspects, and advantages of the apparatus and methods of the present invention will become better understood with regard to the following description, appended claims, and accompanying drawings where:

FIG. 4 illustrates another embodiment of securing graft material to the stent structure of an intraluminal stent graft using heated rivets and washers according to the invention.

DETAILED DESCRIPTION OF THE INVENTION

The systems and methods of the invention are applicable to intraluminal devices such as stent grafts having graft material secured to a stent structure for emplacement in the vasculature or other anatomical passageway of a patient, although the focus of the description herein is directed primarily to intraluminal devices such as stent grafts for use in treating or repairing abdominal aortic aneurysms or the like.

Figure 1:
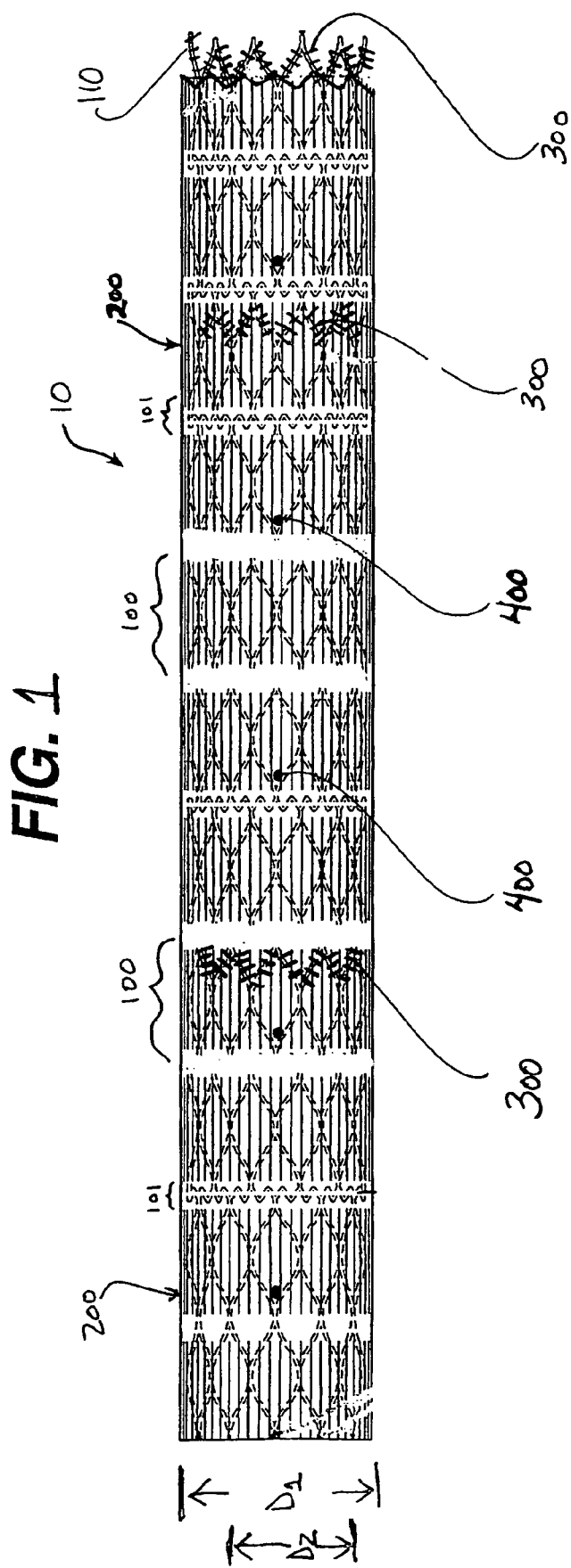
FIG. 1 illustrates an intraluminal device having graft material secured thereto.

FIG. 1 illustrates an exemplary intraluminal device 10. The intraluminal device 10 comprises one or more stent segments 100 having graft material 200 secured thereto. Each stent segment 100 is further comprised of a plurality of struts 110 and longitudinally adjacent stent segments 100 to determine a length of the intraluminal device 10. The longitudinally adjacent stent segments 100 may be interconnected using a connecting member 101, may be non-connected to one another by omission of the connecting member 101, or may be a combination thereof as shown in FIG. 1, to add further dexterity to the intraluminal device 10.

The graft material 200 is comprised of highly durable, non-transparent, biocompatible materials such as, for example, woven polyester, Dacron™, Teflon™, Dyneema, ePTFE, polyurethane or other such materials known to the artisan. The graft material 200 is secured to one or more stent segments 100. The graft material 200 is connected to the intraluminal device 10 by either monofilament or multi-filament sutures 300 provided on alternating struts 110 of at least one segment 100, by heated rivets and washers 400 at or near one or more apexes of at least one segment 100, or by a combination thereof. The sutures 300 are preferably comprised of highly durable, biocompatible materials such as, for example, polyester, Dacron™, Teflon™, Dyneema, ePTFE, polyurethane or other known or later developed material, or combinations thereof, suitable for use as a suture in the discretion of the artisan. Radiopaque materials, such as gold, platinum, platinum with iridium, tantalum, or the like, may also comprise a portion of the graft materials or sutures to aid visualization of the stent graft during delivery and emplacement thereof into a vessel or other passageway in a patient.

As shown in FIG. 1, the intraluminal device 10 has a first diameter D1 when in an expanded, i.e., non-crimped, state. Prior to insertion into the vasculature or other anatomical passageway of a patient, the intraluminal device 10 is crimped to exhibit a second diameter D2 that is smaller than the first diameter D1, as the artisan should readily appreciate. The intraluminal device 10, stent segments 100 and connecting members 101 are preferably made from self-expanding materials such as Nitinol, so as to readily accommodate the first diameter D1 and the second diameter D2. Alternatively, the intraluminal device 10, stent segments 100 and connecting members 101 are made from other independently expandable material such that, after insertion to an intended treatment site, the intraluminal device 10 is expanded from its first diameter D1 to its second diameter D2 by a balloon catheter, for example. The expandable aspects of the intraluminal device 10 are generally known and practiced in the art. The diameters of the intraluminal device 10 will vary according to the materials used and the medical and physiological conditions for which the intraluminal device 10 is to be used. The intraluminal device 10 may provide a single longitudinal axis, as generally shown in FIG. 1, or may include bi-furcated legs as is conventionally practiced in the art for the treatment of abdominal aortic aneurysms, or the like, in particular.

FIG. 1 shows the graft material 200 secured to an external surface of the stent segments 100. The graft material 200 can also, or alternatively, be secured to an internal surface of the stent segments 100. In any event, the graft material 200 is secured to the stent segments 100 by stitches 300 arranged in a staggered or spaced pattern enabling interdigitation of the stitches 300 when the stent segments 100 are in the crimped state according to one embodiment of the systems and methods of the invention, as described in further detail hereinbelow with respect to FIGS. 2-3B. Alternatively, the graft material 200 is secured to the stent segments 100 by heated rivet sutures and washers 400 according to another embodiment of the systems and methods of the invention, as described in further detail hereinbelow with respect to FIG. 4. A still further alternative secures the graft material 200 to the stent segments 100 using a combination of the stitches 300 and the heated suture rivets formed at opposite ends of a suture threaded through a respective preformed hole in the stent segment 100 and a washer 400, as described in further detail hereinbelow with respect to FIG. 5. One end of the graft material 200 is cutaway in FIG. 1 to better illustrate the stitch pattern of the stitches 300 on the alternating struts 110, whereas in practice the graft material 200 is actually secured to the stent segments 100 by the stitches 300.

Figure 2:
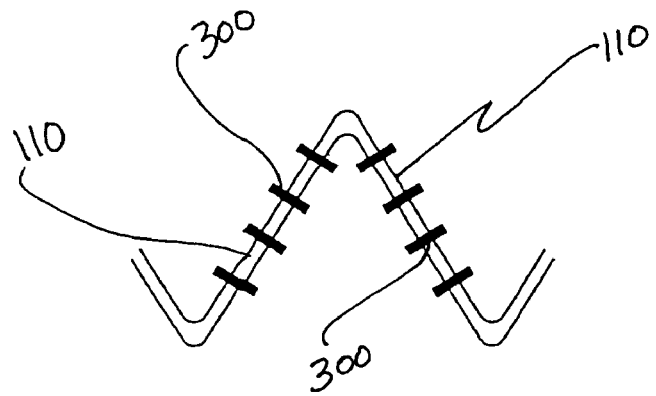
FIG. 2 illustrates a 4:4 blanket stitch ratio for securing graft material to the stent structure of an intraluminal stent graft.

FIG. 2 illustrates schematically a set of stitches 300 blanket stitched onto alternating struts 110 of a stent segment 100 of the intraluminal device 10, for example. Each strut 110 includes four stitches 300 (represented by the solid lines transverse to each of the respective struts 110). While this 4:4 stitch ratio tends to provide good securement of graft material to a stent, the alignment of the stitches in this 4:4 stitch ratio also tends to impede the stent from crimping to a sufficiently smaller diameter D2 as desired for insertion of the stent to the intended treatment site. This impairment occurs because the stitches of the 4:4 stitch ratio tend to contact one another when crimping beyond a certain point is attempted. The crimped diameter of the stent is limited as a result. The desired insertion and delivery diameter D2 of a stent is thus difficult to achieve using the 4:4 stitch ratio depicted in FIG. 2 without risking damage to the graft material, the stitches, or portions of the underlying stent.

Figure 3A:
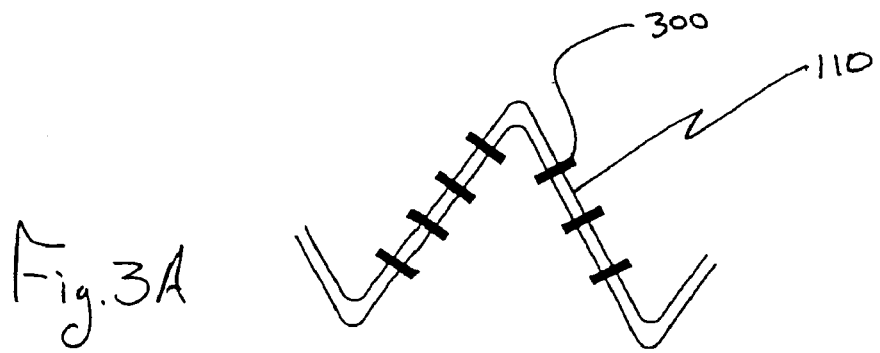
FIGS. 3A and 3B schematically illustrate a staggered blanket stitch ratio for securing graft material to a stent structure in an expanded and crimped state, respectively, according to the invention.
Figure 3B:
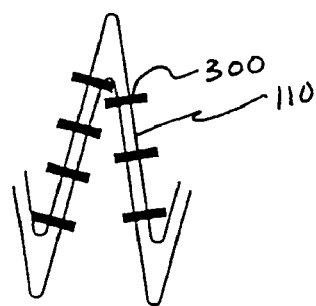

FIG. 3A and FIG. 3B illustrate schematically a set of stitches 300 blanket stitched onto a pair of alternating struts 110 of a stent segment 100 of the intraluminal device 10, for example, according to one embodiment of the systems and methods of the invention. In particular, FIG. 3A illustrates schematically a 3:4 ratio of stitches 300 on a pair of alternating struts 110 as the stent segment 100 is in its expanded state, whereas FIG. 3B illustrates the 3:4 ratio of stitches 300 on the pair of alternating struts 110 as the stent segment 100 is in its crimped state. Of course, as the artisan will readily appreciate, longer stents comprised of longer struts tend to have higher stitch ratios. For example, the even:odd ratio, or vice versa, ratio of blanket stitches provided on the alternating struts is ideally 3:4 stitches for stent grafts having diameters less than 14 mm. The even:odd ratio, or vice versa, ratio of blanket stitches provided on the alternating struts is ideally 4:5 or 5:6 for larger diameter stent grafts having diameters between 14 mm to 30 mm. The even:odd ratio, or vice versa, ratio of blanket stitches provided on the alternating struts is ideally 6:7 or greater, depending on the application, for stent grafts having diameters greater than 30 mm. The blanket stitch length is based on the length of the stent strut that is being stitched along. The stitch ratio per alternating strut helps to accommodate crimping of the stent more fully. Of course, other ratios are contemplated and determined according to stent graft length or other medical and physiological needs.

As shown in FIGS. 3A and 3B, the graft material 200 is secured to the stent segment 100 by three stitches along one strut 110 and by four stitches along the neighboring strut 110 within a stent segment 100 of the intraluminal device 10. Although the stitch ratio is shown as a 3:4 stitch ratio in FIGS. 3A and 3B, other stitch ratios are contemplated as should be readily appreciated by the artisan, provided such ratio provides a staggered stitch pattern enabling the interdigitation of the stitches 300 on the alternating struts 110 of the stent segment 100 when the intraluminal device 10 is crimped. As a result, the intraluminal device 10 more readily accommodates crimping to its smaller insertion diameter D2 for insertion and delivery of the stent to an intended treatment site without compromising flexibility and radial stiffness of the stent.

The stitches 300 may be provided on every segment 100 of the intraluminal device 10, or may be provided on only some or one of the segments 100 of the intraluminal device 10 as determined sufficient to achieve the intended securement of the graft material 200 to the stent segments 100. The stitches 300 may be secured to each strut 110 within a stent segment 100 of an intraluminal device 10, or may be secured to only some or one of the struts 110 within a stent segment 110 of the intraluminal device 10 as deemed sufficient to achieve the intended securement of the graft material 200 to the stent segments 100 of the intraluminal device 10.

Of course, although not shown, the stitch ratio can instead be an even:even ratio provided that the spacing between the even number of stitches on one strut is complementarily spaced with the even number of stitches on the alternating neighboring struts to enable the intended interdigitation of the even:even ratio of stitches. Because the spacing of such even: even stitch ratios to accommodate the intended interdigitation of stitches is more difficult to co-ordinate, the even:odd stitch ratio on alternating struts in a segment is preferred.

Because current devices for minimally invasive treatment of abdominal aortic aneurysms tend to be large, for example, in the range of 18 Fr to 24 Fr, the stent grafts having interdigitated stitch ratios, as described herein, provide lower profile stent grafts that contribute to easier insertion and delivery of the stent grafts to an intended treatment site. Stent grafts having such interdigitated stitch ratios can have crimped profiles of 0.109 inch +/−0.001 inch, or smaller, for example, which tends to be produced from smaller tubes than existing devices are cut from or wire formed from. At the same time, improved and reliable securement of the graft material 200 to the stent segments 100 of the intraluminal device 10 is achieved using the techniques detailed herein.

FIG. 4 illustrates another embodiment of securing graft material to a stent to form an intraluminal stent graft according to the systems and methods of the invention. As shown in FIG. 4, wherein like numerals are used for like parts as in previously described embodiments herein, the graft material 200 is secured to the stent segements 100 of the intraluminal device 10 by a suture 500 (only the ends 501 and 502 of which are shown) threaded through at least one preformed hole 150 formed in a portion of the stent segment 100, the graft material 200, and a corresponding washer 400 overlying the graft material 200 on an exterior surface of the stent 10. The suture 500 may be a monofilament or a multifilament, having ends 501 and 502 that are knotted and terminated by heat to form a rivet larger than the opening provided through the preformed holes 150 or washers 400 through which the suture 500 is threaded. The ends 501 and 502 of the sutures 500 are knotted and terminated by heat to form rivets so that the neither of the ends 501, 502 of the suture 500 passes through the respective preformed holes 150, the graft material 200 or the washer 400 through which the suture 500 was threaded. In this way, the graft material 200 ideally is secured to the stent segment 100. The washer 400 thus has an opening 401 through which the filament suture 500 is threaded such that one end 501 of the suture 500 extends within an interior cavity of the stent segment 100, and an opposite end 502 of the suture 500 remains outside the external surface of the stent segment 100. Securing the graft material 200 in this manner enables the graft material 200 to move with the stent segment 100 between the expanded diameter D1 and the crimped diameter D2 while still maintaining the graft material 200 in place as desired about the intraluminal device 10 during insertion, delivery and deployment thereof.

Preferably, the end 501 of each suture 500 that is within the interior cavity of the stent segment 100 is heated first, whereafter the external end 502 of each suture is then heated. The washer 400 can be emplaced before or after threading the suture 500 through the graft material 200. Heating the interior end 501 of each suture 500 is considered the easier method of securing the graft material 200 to the stent segment 100 according to this embodiment. Alternatively, the sequence can be inversely performed, whereby the external end 502 of each suture 500 is heated first, and then the internal end 501 of each suture 500 is heated such that the graft material 200 is positioned therebetween the heat riveted ends 501, 502 of the suture to secure the graft material 200 to the stent segment 100 of the intraluminal device 10.

Although the washer 400 is shown on the external surface of the graft material 200 and stent segment 100, which is preferred, the washer 400 can be emplaced on the internal surface of the graft material 200 and stent segment 100 if desired. In either case, the washer 400 is preferably comprised of radiopaque material, such as tantalum, tungsten, gold, platinum, or other known or later developed radiopaque materials to enhance visualization of the stent graft during insertion, delivery and deployment thereof.

Each suture 500, preformed hole 150 and washer 400 combination is ideally placed at or near an apex, or junction, of struts 110 of a stent segment 100 of the intraluminal device 10, as shown, for example, in FIG. 4, although other locations are readily achievable by altering the location of the preformed hole 150 to elsewhere in or along the struts of the stent. Further, although the struts 110 shown in FIG. 4 are connected, the artisan will readily appreciate that non-connected struts may also comprise the stent, wherein the combination of sutures 500, preformed holes 150 and washers 400 will secure graft material 200 to the stent as described otherwise herein.

For illustration only, FIG. 4 shows two washers 400 in place along an exterior surface of the stent segment 100 and graft material 200 with a heated rivet 502 ideally precluding the suture 500 from passing through the washer 400, whereas FIG. 4 also shows two preformed stent holes 150 as if the graft material 200 is removed. In practice, the graft material 200 tends to cover the preformed holes 150, even where sutures 500 are not threaded through all of such preformed holes 150. Moreover, where the sutures 500 are threaded through such preformed holes 150, then heated rivets 501 of FIG. 4, ideally preclude the suture 500 from passing through the respective preformed hole 150. In this manner, the graft material 200 is able to move as the stent is crimped from an expanded diameter D1 to a smaller insertion diameter D2, as in earlier described embodiments. The number of suture 500, preformed hole 150 and washer 400 combinations that are used to secure the graft material 200 to the stent segment 100 is limited by the number of segments 100 and struts 110 that exist within an intraluminal device 10, whereby the more suture 500, preformed hole 150 and washer 400 combinations that are used the better the graft material 200 tends to be secured to the stent segment 100, although as few as one suture 500, preformed hole 150 and washer 400 combination could be used. Securing the graft material 200 to the stent segment 100 to comprise the stent graft as shown in FIG. 4 thus minimizes inadvertent and undesirable micro-motions of the graft material 200 relative to the stent segment 100 of an intraluminal device 10 while still providing good flexibility and radial stiffness in a stent having a low insertion and delivery profile.

Figure 5:
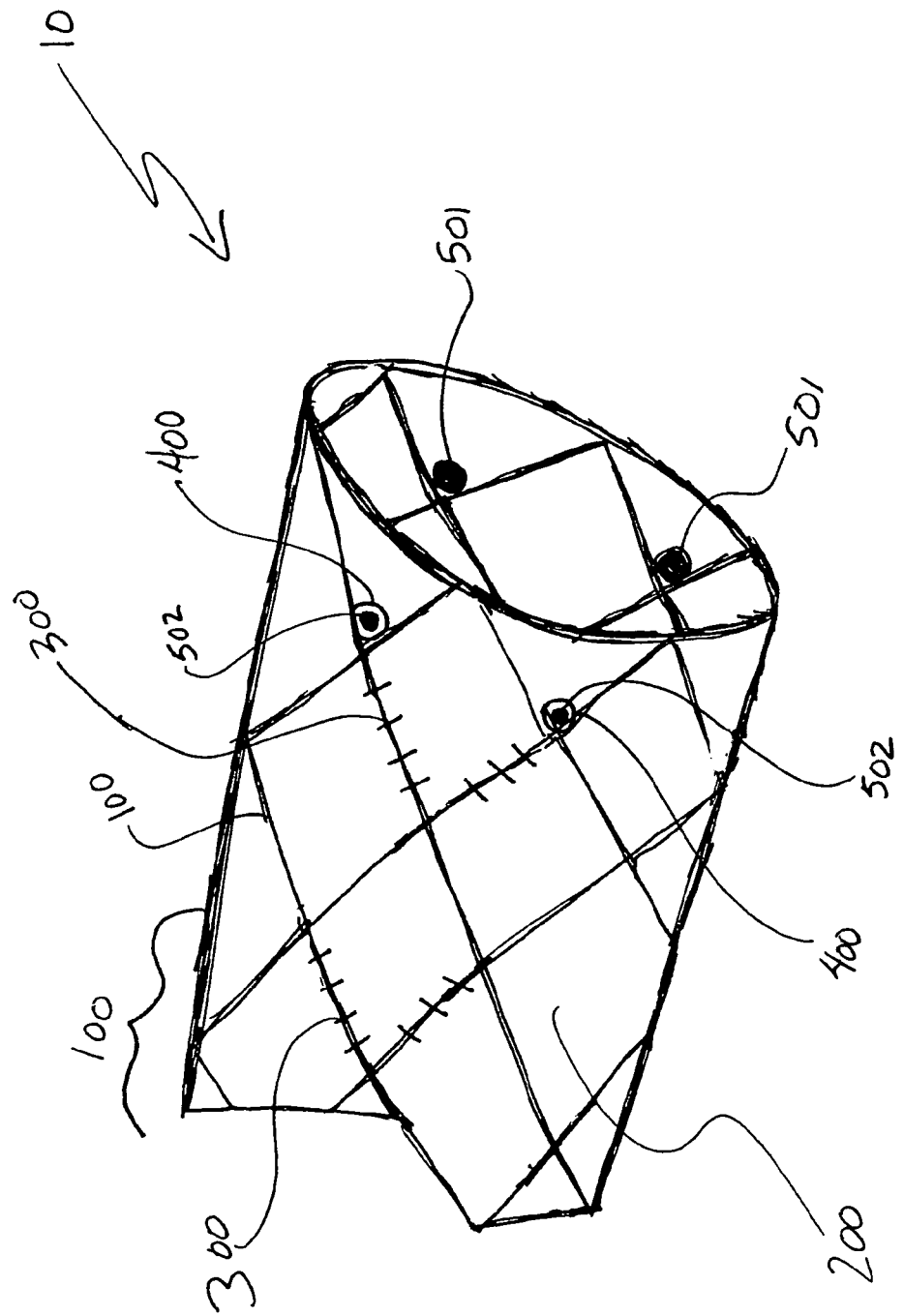
FIG. 5 illustrates an embodiment of securing graft material to the stent structure of an intraluminal stent graft using a combination of the staggered blanket stitch ratio and the heated rivet and washers according to the invention.

FIG. 5 illustrates an alternative embodiment for securing graft material to a stent to comprise an intraluminal stent graft device according to the systems and methods of the invention. As shown in FIG. 5, the interdigitated stitch ratio of the first embodiment (FIGS. 2-3B) described hereinabove is combined with the suture and washer combination of the second embodiment (FIG. 4) described hereinabove. Thus, some of the alternating struts 110 are provided with interdigitable stitches 300 to secure the graft material 200 to the stent segment 100 while enabling the intraluminal device 10 to assume a low profile in its crimped state, and other struts 110 of the stent segment 100 are provided with a suture 500, preformed hole 150 and washer 400 combination to also secure the graft material 200 to the stent segment 100. This hybrid technique shown in FIG. 5 also enables the intraluminal device 10 to assume a low profile in its crimped state. Upon delivery to the intended treatment site, the stent graft is deployed to its expanded diameter D1 in conventional manner.

The various exemplary embodiments of the invention as described hereinabove do not limit different embodiments of the systems and methods of the invention. The material described herein is not limited to the materials, designs or shapes referenced herein for illustrative purposes only, and may comprise various other materials, designs or shapes suitable for the systems and methods described herein, as should be appreciated by the artisan.

While there has been shown and described what is considered to be preferred embodiments of the invention, it will, of course, be understood that various modifications and changes in form or detail could readily be made without departing from the spirit or scope of the invention. It is therefore intended that the invention be not limited to the exact forms described and illustrated herein, but should be construed to cover all modifications that may fall within the scope of the appended claims.

What is claimed is:

1. A stent graft comprising:
   an expandable stent having at least one segment comprised of alternating struts, an expanded diameter and a crimped diameter, wherein the alternating struts of each segment form an external surface and an internal cavity of the stent;
   graft material secured to the stent and enabling the stent graft to move between the expanded diameter and the crimped diameter;
   a series of interdigitable stitches securing the graft material to at least some of the alternating struts and providing a low profile to the stent graft when in the crimped diameter, wherein the interdigitable stitches comprise an even:odd stitch ratio;
   at least one suture threaded through the graft material and at least one preformed hole in a portion of the stent; and
   at least one washer corresponding to each of the at least one suture, whereby a first end of each suture is heated to expand against a respective one of the at least one preformed hole of the stent, and a second end of each suture is heated to expand against a respective one of the at least one washer being located between the second end of a respective one of at last one suture and the graft material.

2. The stent graft of claim 1, wherein the expandable stent is comprised of self expanding material.

3. The stent graft of claim 2, wherein the self-expanding material is at least partially comprised of Nitinol.

4. The stent graft of claim 1, wherein the expandable stent is a balloon expandable stent.

5. The stent graft of claim 1, wherein the graft material is comprised of bio-compatlble materials.

6. The stent graft of claim 5, wherein the biocompatible materials are at least one of woven polyester, Dacron, Teflon, Dyneema, ePTFE, and polyurethane.

7. The stent graft of claim 1, wherein the even:odd stitch ratiois 3:4.

8. The stent graft of claim 1, wherein the even:odd stitch ratio is other than 3:4.

9. The stent graft of claim 1, wherein the interdigitable stitches comprise an even:even stitch ratio sufficiently spaced along the at least some of the alternating shuts so as not to contact one another when the stent is in the crimped diameter.

10. The stent graft of claim 1, wherein the alternating struts are interconnected, non-connected, or a combination thereof.

11. The stent graft of claim 1, wherein the suture is a monofilament.

12. The stent graft of claim 1, wherein the suture is a multi-filament.

* * * * *